US012256927B1

(12) United States Patent
Zeiner et al.

(10) Patent No.: US 12,256,927 B1
(45) Date of Patent: Mar. 25, 2025

(54) IMPLANTABLE ADJUNCT TO ASSURE FULL CUTTING

(71) Applicant: CILAG GMBH INTERNATIONAL, Zug (CH)

(72) Inventors: Mark Zeiner, Loveland, OH (US); Omar McGiveron, Cincinnati, OH (US); Michael J. Vendely, Lebanon, OH (US); Sarah Scully, Cincinnati, OH (US); John Schulte, Cincinnati, OH (US); Madelaine Franzoni, Cincinnati, OH (US); Brody Frost, Fairfield, OH (US)

(73) Assignee: CILAG GMBH INTERNATIONAL, Zug (CH)

( * ) Notice: Subject to any disclaimer, the term of this patent is extended or adjusted under 35 U.S.C. 154(b) by 0 days.

(21) Appl. No.: 18/395,133

(22) Filed: Dec. 22, 2023

(51) Int. Cl.
*A61B 17/072* (2006.01)
*A61B 17/00* (2006.01)
*A61B 17/068* (2006.01)

(52) U.S. Cl.
CPC ...... *A61B 17/072* (2013.01); *A61B 17/07292* (2013.01); *A61B 2017/00526* (2013.01); *A61B 17/068* (2013.01); *A61B 17/07207* (2013.01); *A61B 2017/07214* (2013.01); *A61B 2017/0725* (2013.01); *A61B 2017/07285* (2013.01)

(58) Field of Classification Search
CPC .......... A61B 17/068; A61B 17/072; A61B 17/07207; A61B 17/07292; A61B 17/115; A61B 2017/00526; A61B 2017/07214; A61B 2017/07285; A61B 2017/0725

USPC ...... 227/19, 175.1, 176.1, 180.1; 606/1, 139, 606/219
See application file for complete search history.

(56) References Cited

U.S. PATENT DOCUMENTS

| | | | | |
|---|---|---|---|---|
| 7,810,692 B2* | 10/2010 | Hall | ............ | A61B 17/07207 227/176.1 |
| 8,011,555 B2* | 9/2011 | Tarinelli | ............ | A61B 17/07207 227/176.1 |
| 8,016,177 B2* | 9/2011 | Bettuchi | ............ | A61B 17/07207 227/181.1 |
| 8,062,330 B2* | 11/2011 | Prommersberger | ............ | B29C 39/123 606/151 |
| 8,157,151 B2* | 4/2012 | Ingmanson | ............ | A61B 17/068 227/176.1 |
| 8,584,920 B2* | 11/2013 | Hodgkinson | ............ | A61B 17/07292 227/176.1 |
| 8,668,129 B2* | 3/2014 | Olson | ............ | A61B 17/115 227/19 |
| 8,893,949 B2* | 11/2014 | Shelton, IV | ............ | A61B 17/1155 227/176.1 |
| 9,198,662 B2* | 12/2015 | Barton | ............ | A61B 17/0643 |
| 9,402,627 B2* | 8/2016 | Stevenson | ............ | A61B 17/105 |
| 9,610,080 B2* | 4/2017 | Whitfield | ............ | A61B 17/07292 |
| 9,675,351 B2* | 6/2017 | Hodgkinson | ............ | A61B 17/1155 |
| 10,293,553 B2* | 5/2019 | Racenet | ............ | B29C 66/727 |
| 10,499,918 B2* | 12/2019 | Schellin | ............ | A61B 17/07292 |
| 10,842,485 B2* | 11/2020 | Hodgkinson | ............ | A61B 17/068 |

(Continued)

*Primary Examiner* — Scott A Smith
(74) *Attorney, Agent, or Firm* — TROUTMAN PEPPER LOCKE LLP

(57) ABSTRACT

Staple cartridge systems with implantable adjuncts and retainers are disclosed. The staple cartridge systems ensure the full-cutting of the implantable adjuncts through the structure/manufacturing of the implantable adjuncts and the retainers.

20 Claims, 10 Drawing Sheets

(56) References Cited

U.S. PATENT DOCUMENTS

| | | | |
|---|---|---|---|
| 11,026,686 B2* | 6/2021 | Aranyi | A61B 17/07292 |
| 11,154,297 B2* | 10/2021 | Swayze | A61B 17/0643 |
| 11,426,163 B2* | 8/2022 | Williams | A61B 17/1155 |
| 11,678,879 B2* | 6/2023 | Baril | A61B 17/072 |
| | | | 227/175.1 |
| 11,801,052 B2* | 10/2023 | Baril | A61B 17/07292 |
| 2011/0215133 A1* | 9/2011 | Aranyi | A61B 17/07207 |
| | | | 227/176.1 |
| 2023/0111108 A1* | 4/2023 | Baril | A61B 17/07207 |
| | | | 227/176.1 |

* cited by examiner

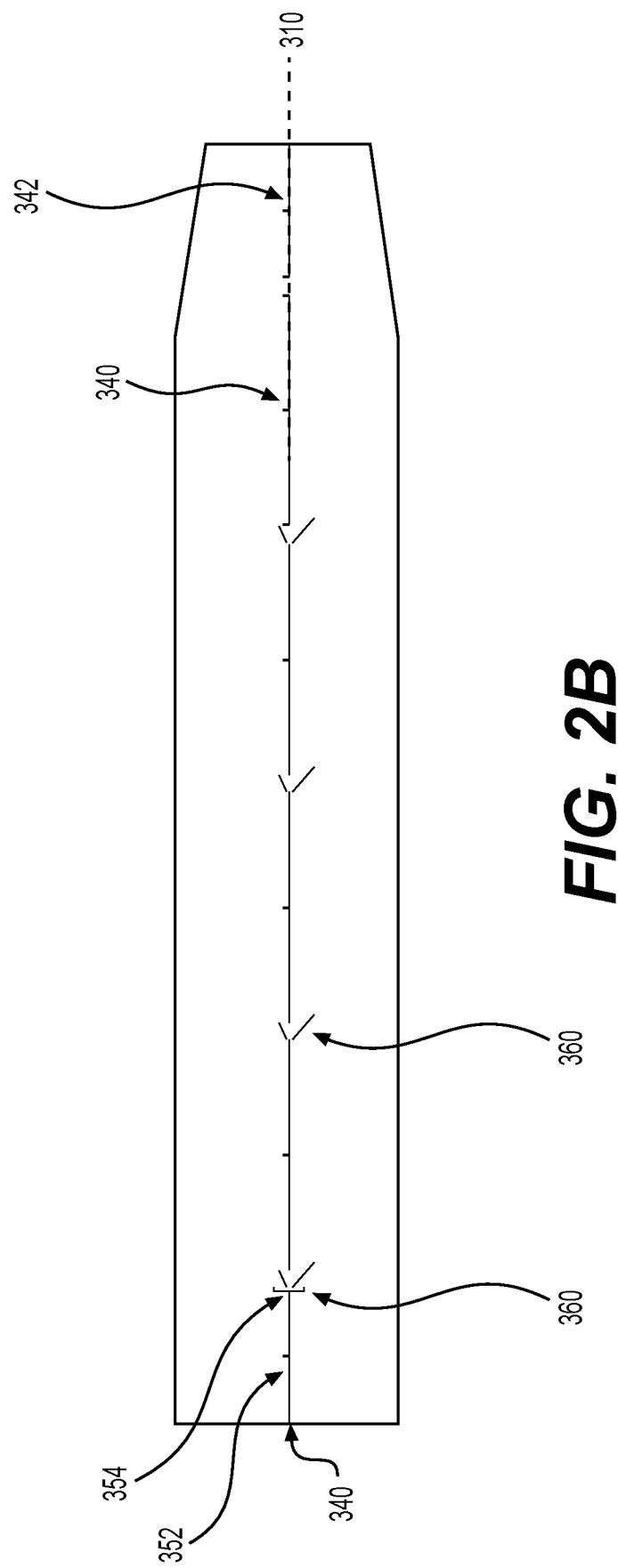

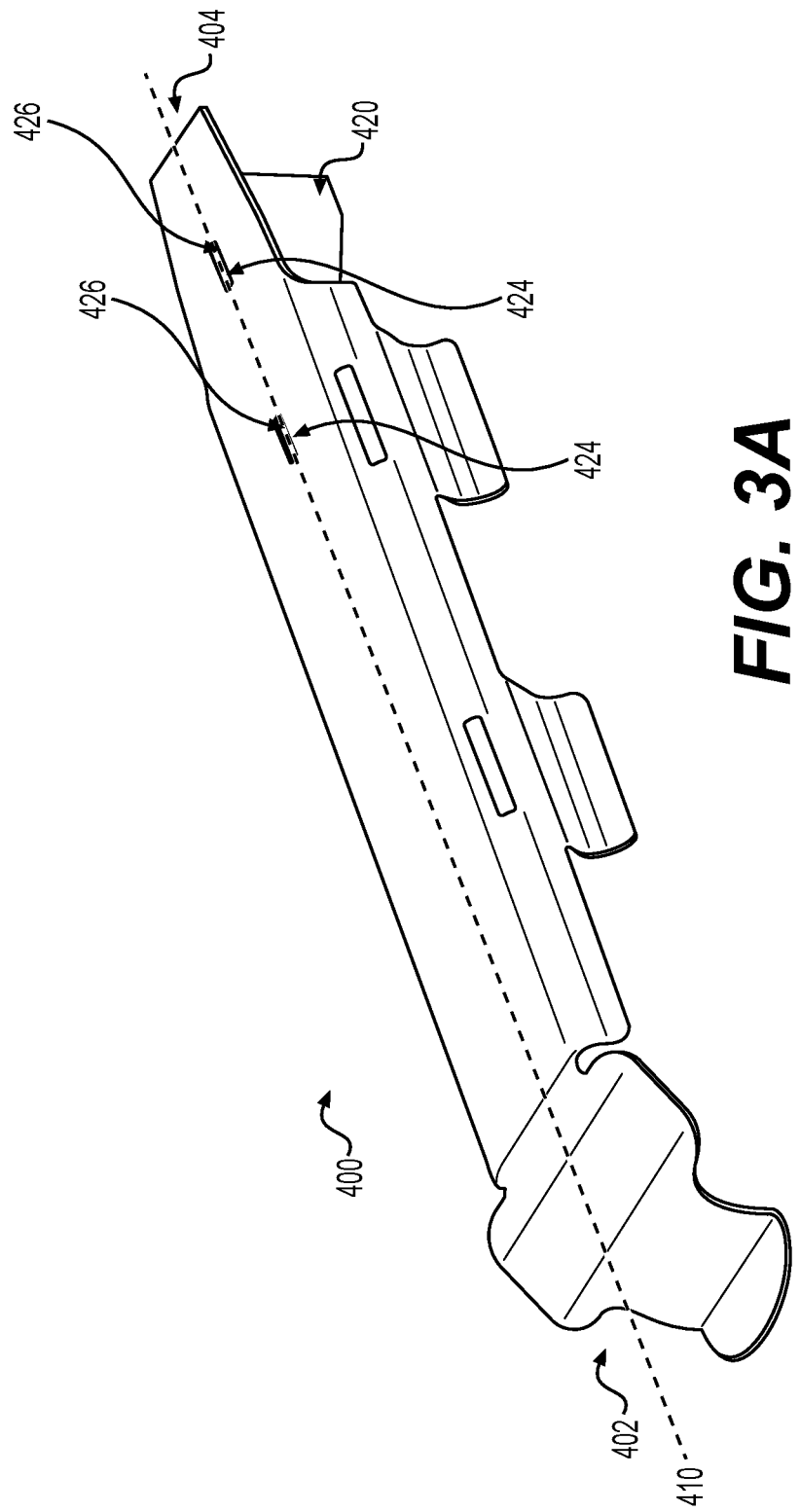

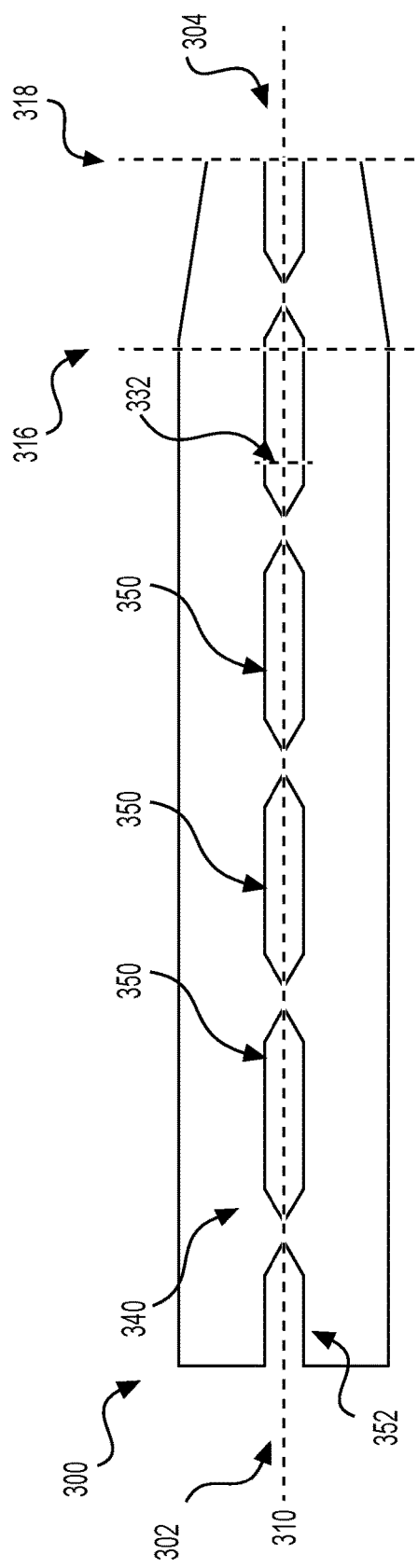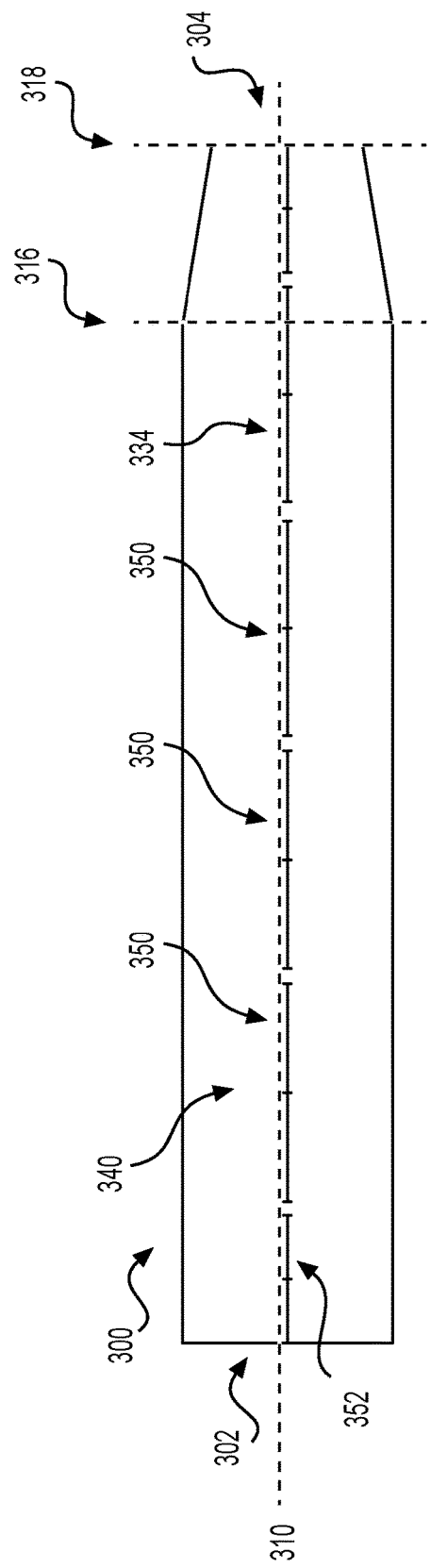

600

| |
|---|
| ASSEMBLE AN IMPLANTABLE ADJUNCT ONTO A DECK OF AN ELONGATE BODY, THE IMPLANTABLE ADJUNCT COMPRISING A DISTAL END AND A TAPERED PROXIMAL END, THE TAPERED PROXIMAL END HAVING A WIDTH THAT IS WIDER AT A DISTAL END OF THE TAPERED PROXIMAL END THAN THE WIDTH AT A PROXIMAL END OF THE TAPERED PROXIMAL END |

~602

| |
|---|
| CUT A KNIFE SLOT DEFINING SEVERAL SLITS IN THE IMPLANTABLE ADJUNCT ALONG A LONGITUDINAL AXIS THAT EXTENDS THE WIDTH OF THE IMPLANTABLE ADJUNCT, THE KNIFE SLOT COMPRISING A FIRST WIDTH, THE FIRST WIDTH BEING LARGER THAN THE WIDTH OF A CENTER RIB EXTENSION OF A STAPLE CARTRIDGE |

~604

| |
|---|
| COMPRESS THE IMPLANTABLE ADJUNCT SUCH THAT THE KNIFE SLOT HAS A SECOND WIDTH, THE SECOND WIDTH OF THE KNIFE SLOT BEING SMALLER THAN THE FIRST WIDTH OF THE KNIFE SLOT. |

IMPLANTABLE ADJUNCT TO ASSURE FULL CUTTING

FIELD

The present disclosure generally relates to staple cartridges with implantable adjuncts and retainers. More specifically, the present disclosure relates to implantable adjuncts having perforations along the knife slot and a retainer with a center rib extension to ensure full cutting of the implantable adjunct on a staple cartridge.

BACKGROUND

Stapling is a crucial aspect of many surgical procedures, such as gastrointestinal, thoracic, and gynecological surgeries. Staple cartridges used in stapling procedures may include an implantable adjunct on the deck of the cartridge and a retainer coupled to the cartridge as well. It is important to ensure that the implantable adjunct is fully split into two during the removal of the retainer from the staple cartridge.

SUMMARY

It is an object of the present designs to provide devices and methods to meet the above-stated needs. The designs can be for systems and devices for assuring the full cutting of an implantable adjunct on a staple cartridge before being used in surgery.

The disclosed technology includes a staple cartridge. The staple cartridge comprises an elongate body. The elongate body comprising a deck and defining a plurality of staple pockets which are accessible via an opening defined by the deck. The staple cartridge further comprises an implantable adjunct disposed on the deck of the elongate body. The implantable adjunct comprising a distal end, a proximal end, and a knife slot positioned along a longitudinal axis of the implantable adjunct. The knife slot comprises a plurality of slits defining a perforation in the implantable adjunct and a transverse cut transversely intersecting a distal most slit of the plurality of slits at a proximal end of the distal most slit of the knife slot.

The disclosed technology further includes a method for producing an implantable adjunct. The method includes the step of assembling an implantable adjunct onto a deck of an elongate body. The implantable adjunct comprising a distal end and a tapered proximal end. The tapered proximal end having a width that is wider at a distal end of the tapered proximal end. The method further includes the step of cutting a knife slot comprising a plurality of slits in the implantable adjunct to define a perforation along a longitudinal axis that extends the length of the implantable adjunct. The knife slot comprises a first width, the first width being larger than the width of a center rib extension of a retainer. The method further includes the step of compressing the implantable adjunct such that the knife slot has a second width, the second width being smaller than the first width of the knife slot.

The disclosed technology further includes an implantable adjunct for use with a staple cartridge. The implantable adjunct comprises a distal end comprising a constant width along a major length of the distal end. The implantable adjunct further includes a tapered proximal end comprising a distal end and a proximal end, and having a width at the distal end that is wider than a width at the proximal end. The implantable adjunct further includes a knife slot disposed within the implantable adjunct and positioned along a longitudinal axis of the implantable adjunct. The knife slot is configured to have a width that is a predetermined distance greater than zero. The implantable adjunct is configured to compensate for a varying thickness of target tissue of a patient that is being stapled and comprises a bio-degradable material.

Other aspects of the present disclosure will become apparent upon reviewing the following detailed description in conjunction with the accompanying figures. Additional features or manufacturing and use steps can be included as would be appreciated and understood by a person of ordinary skill in the art.

BRIEF DESCRIPTION OF THE DRAWINGS

The above and further aspects of this invention are further discussed with reference to the following description in conjunction with the accompanying drawings, in which like numerals indicate like structural elements and features in various figures. The drawings are not necessarily to scale, emphasis instead being placed upon illustrating principles of the invention. The figures depict one or more implementations of the inventive devices, by way of example only, not by way of limitation. It is expected that those of skill in the art can conceive of and combine elements from multiple figures to better suit the needs of the user.

FIG. 2B is a top view of an implantable adjunct illustrating angled transverse cuts along the knife slot, according to aspects of the present invention.

FIG. 3A is a perspective view of a retainer for a staple cartridge, according to aspects of the present invention.

FIG. 5A is a top view of an implantable adjunct before compression, according to aspects of the present invention.

FIG. 5B is a top view of an implantable adjunct after it has been compressed, according to aspects of the present invention.

FIG. 6 is a flowchart illustrating a method of producing an implantable adjunct for a staple cartridge, according to aspects of the present invention.

DETAILED DESCRIPTION

Figure 1:
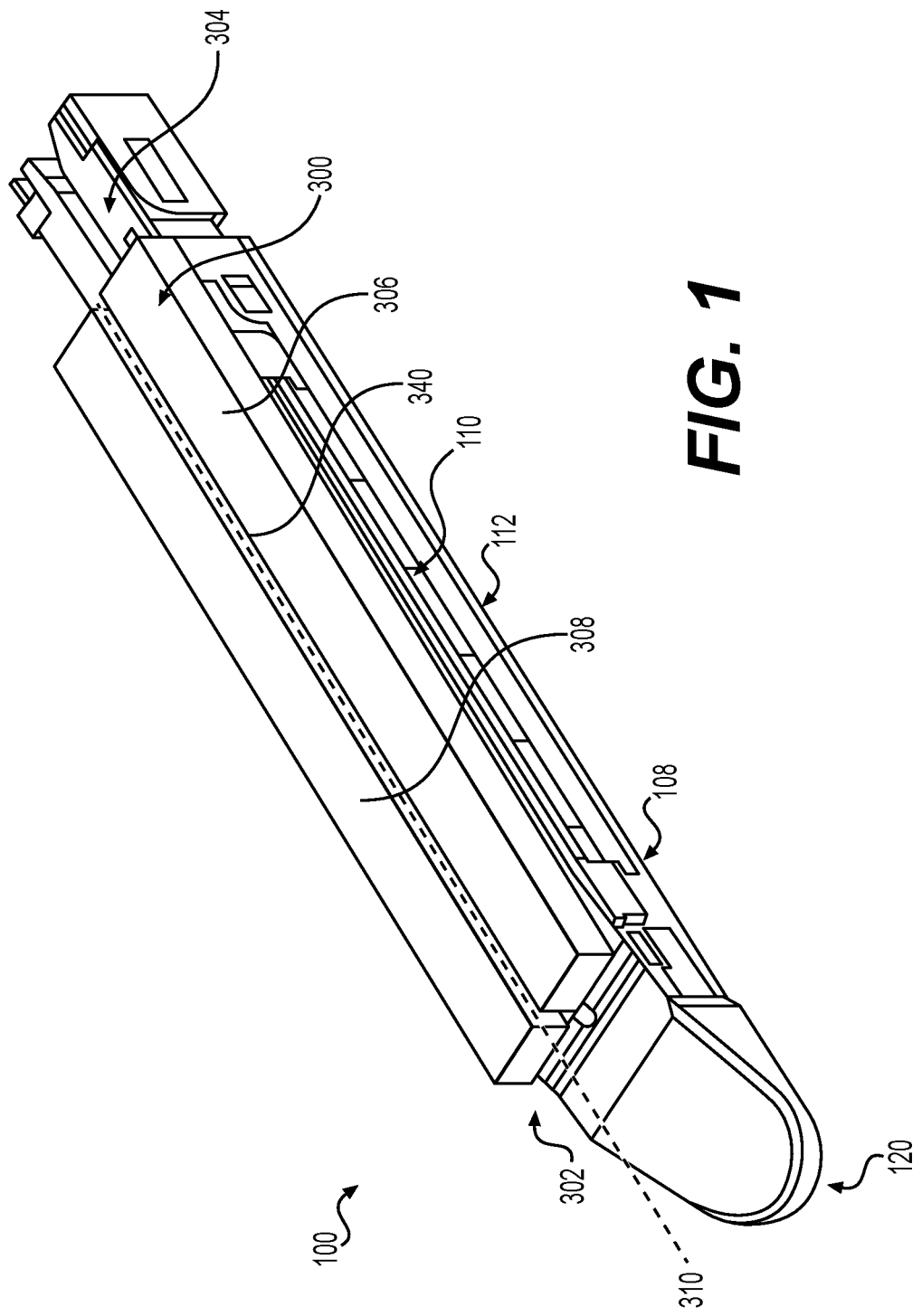
FIG. 1 is a perspective view of a staple cartridge and implantable adjunct without a retainer, according to aspects of the present invention.

Specific examples of the present invention are now described in detail with reference to the Figures, where identical reference numbers indicate elements which are functionally similar or identical. The examples provide solutions for staple cartridge systems that include an implantable adjunct and a retainer comprising a center rib extension. An implantable adjunct can be used in staple cartridge systems and will, as explained above, be compressed then loaded onto the deck of a staple cartridge that is then loaded into a surgical stapler. Prior to installation onto a surgical stapler, a retainer is removed from the staple cartridge and as a result splits the implantable adjunct into two halves. For the sake of manufacturing, a single implantable adjunct component with a knife slot down the center is desired rather than an implantable adjunct split into two separate halves beforehand. Bridges/connections between either side of the implantable adjunct and along the knife slot is also desired to ensure that the implantable adjunct is not split into two halves before it is necessary.

However, these connections can interfere with the center rib extensions of the retainers during installation and removal of the retainers from the staple cartridges. Additionally, as a result of the compression, the knife slot has width of approximately zero and it is required that the center rib extension of the retainer properly align with the knife slot as it is cut. If these connections are not properly severed and the rib extension is not properly aligned during the removal of the retainer, then the staple procedure can be interrupted and can result in a wasted staple cartridge and increased procedural duration. As such, the present staple cartridge system provides solutions to ensure that the connections do not interfere with the retainer during installation and removal and that the implantable adjunct is properly separated into two halves. These systems provide solutions by incorporating a retainer that includes a center rib extension with a sharp edge and an implantable adjunct that has a knife slot comprising a plurality of slits and transverse cuts at each slit to ensure full cutting down the center of the implantable adjunct after the removal of the retainer from the staple cartridge.

The invention is not necessarily limited to the examples described, which can be varied in construction and detail. The terms "distal" and "proximal" are used throughout this description and are meant to refer to positions and directions relative to the handle of a surgical instrument. As such, "distal" or "distally" refer to a position distant to or a direction away from the handle of a surgical instrument (i.e., a direction toward a patient). Similarly, "proximal" or "proximally" refer to a position near or a direction towards the handle of a surgical instrument (i.e., toward an operator of the instrument). Furthermore, the singular forms "a," "an," and "the" include plural referents unless the context clearly dictates otherwise. Furthermore, the term "sharp" to describe the edge of a surface indicates an object having an edge that is capable of cutting or severing a material, surface, or other object. As used herein, the term "slit", or "slits", indicate a long and narrow opening or openings in a material that, once cut, define opposing walls having a separation that is greater than zero.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values±20% of the recited value, e.g. "about 90%" may refer to the range of values from 71% to 99%.

The components described herein can be formed from biocompatible materials using manufacturing methods known to those of skill in the art. For example, and not limitation, the components described herein can be molded from a thermoplastic.

Referring now to the figures, FIG. 1 shows a perspective view of an example staple cartridge 100 including an implantable adjunct 300 that has been split into two halves 306, 308 by a retainer 400 that will be depicted later in FIGS. 3A-4B. As shown, the staple cartridge 100 includes an elongate body 120 having a deck 108 and defining a plurality of staple pockets 110 that are accessible via openings 112 defined by the deck 108 of the elongate body 120. The implantable adjunct 300 is disposed on the deck 108 of the elongate body and comprises a distal end 302, a proximal end 304, and a knife slot 340 positioned along the length of a longitudinal axis 310 that extends the length of the implantable adjunct 300.

Figure 2A:
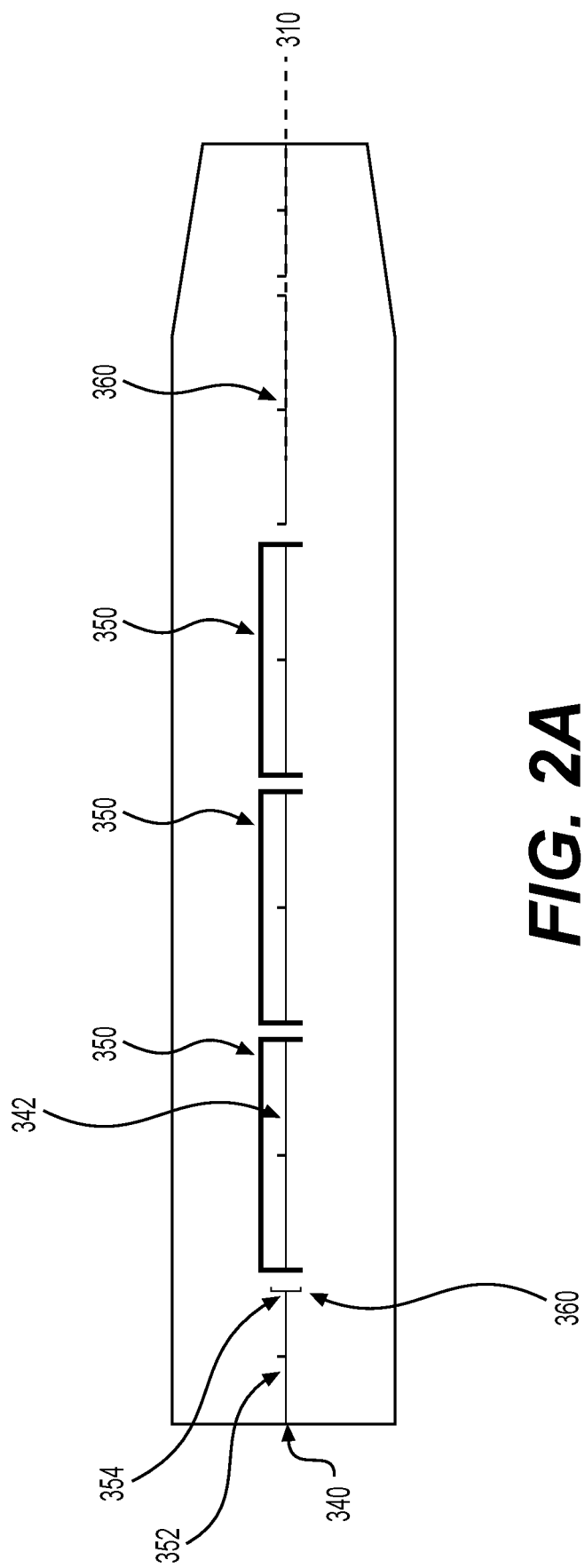
FIG. 2A is a top view of an implantable adjunct illustrating transverse cuts along the knife slot, according to aspects of the present invention.

Turning now to FIGS. 2A-2B, top views of an implantable adjunct 300 comprising transverse cuts 360 are shown. Specifically, FIG. 2A shows a top view of an implantable adjunct 300, and a knife slot 340 positioned along a longitudinal axis 310 of the implantable adjunct 300. The knife slot 340 includes a plurality of slits 350 that define a perforation 342 in the implantable adjunct 300 and a transverse cut 360 that transversely intersects a distal-most slit 352 of the plurality of slits 350 at a proximal end 354 of the slit 352. The knife slot 340 can further include additional transverse cuts 360 at the proximal end 354 of each slit 350 of the plurality of slits 350, each transverse cut 360 transversely intersecting each slit 350 of the plurality of slits 350.

Alternatively, the transverse cut 360 can have an angle that ranges approximately from 70 to 89 degrees when measured from the longitudinal axis 310 of the implantable adjunct 300, as can be seen in FIG. 2B. The implantable adjunct 300 can further include additional transverse cuts 360 disposed at the proximal ends 354 of each slit 350 of the plurality of slits 350. Each transverse cut 360 has an angle that ranges approximately from 70 to 89 degrees when measured from the longitudinal axis 310. The transverse cuts 360 made along the knife slot 340 permit proper alignment of a retainer 400 having a center rib extension 420, as is explained in further detail in FIGS. 3A-3C. By making the transverse cuts 360, one will still be able to properly split an implantable adjunct 300 into two halves 306, 308, even if slightly misaligned as the transverse cuts 360 allow for a larger width of the knife slot 340 to be contacted by the edge of the center rib extension 420. Further, opposing walls that define the slits 350 of the knife slot 340 are configured to touch when the implantable adjunct 300 is disposed on the deck 108 of a staple cartridge 100.

Figure 3B:
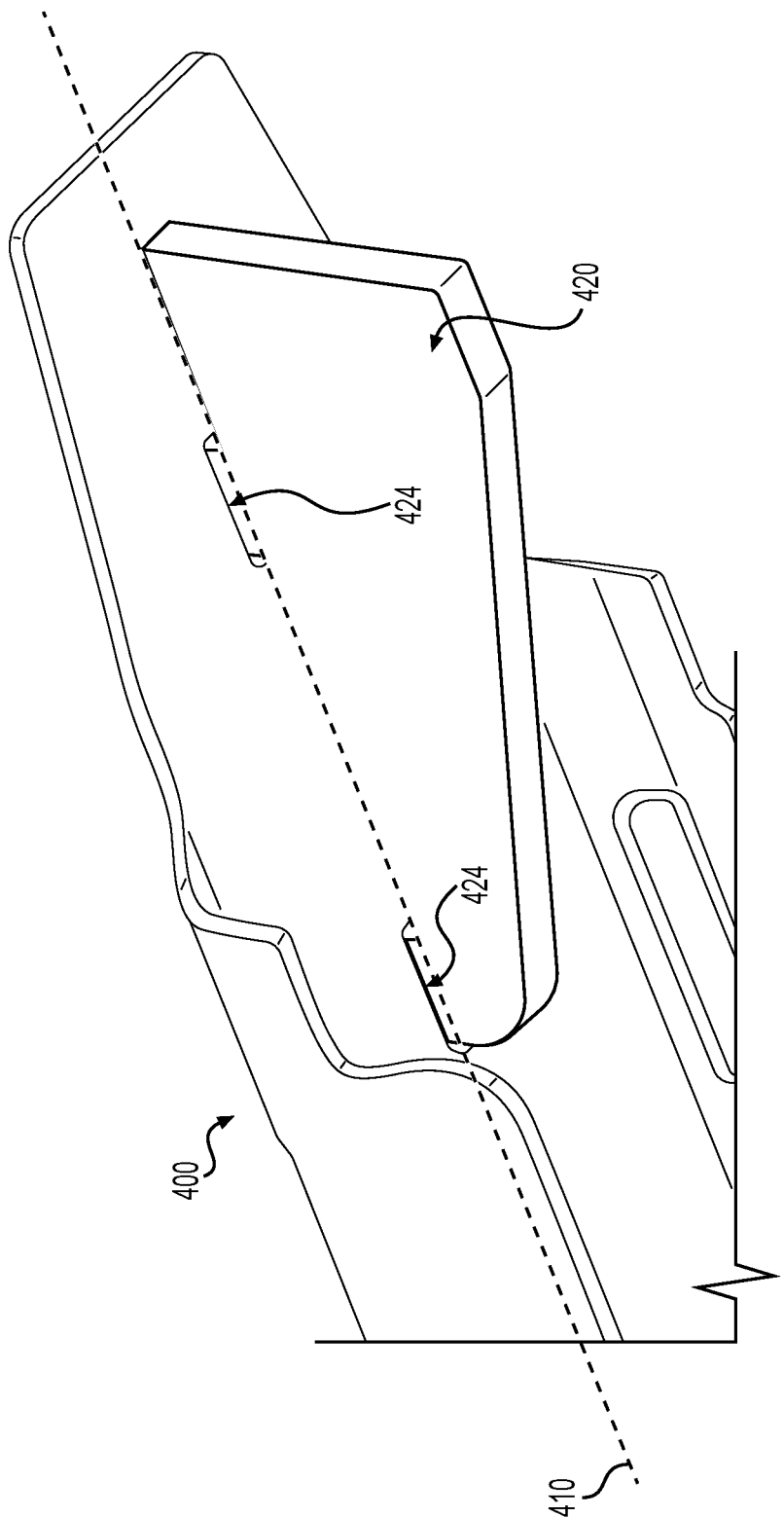
FIG. 3B is a bottom perspective view of the center rib extension that is approximately 25% of the length of the retainer of FIG. 3A, according to aspects of the present invention.
Figure 3C:
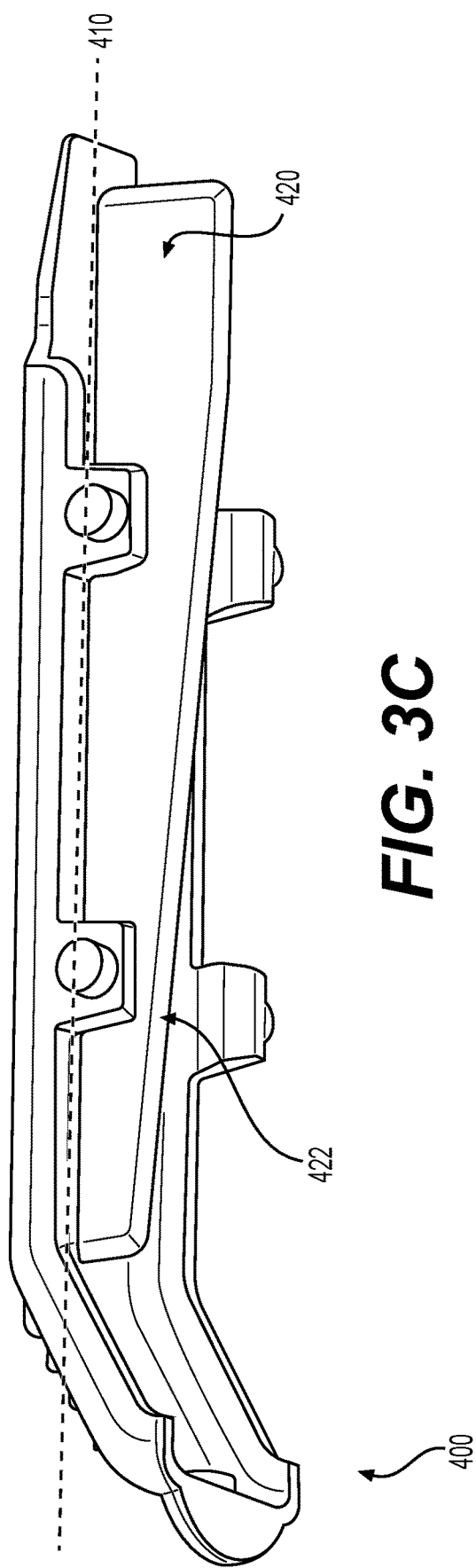
FIG. 3C is another bottom perspective view of a center rib extension that is approximately 75% of the length of a retainer for a staple cartridge, according to aspects of the present invention.

FIGS. 3A-3C show various views of a retainer 400 that is removably connected to an elongate body 120 of a staple cartridge 100. The retainer 400 includes a longitudinal axis 410 that extends the length of the retainer 400, a distal end 402, a proximal end 404, at least two openings 426 formed along the longitudinal axis 410 and adjacent to the proximal end 402, and a center rib extension 420 positioned along the longitudinal axis 410. The center rib extension 420 includes two alignment tabs 424 that protrude from the center rib extension 420 and connect to the two openings of the retainer 400. The center rib extension 420 further includes an edge 422 that tapers on both sides forming a sharp edge 422 along the entire length of the center rib extension 420.

FIGS. 3A and 3B show a retainer 400 that includes a center rib extension 420 comprising a length that is less than or equal to approximately 25% of the length of the retainer 400 measured along the longitudinal axis 410. FIG. 3C shows an alternative embodiment of a center rib extension 420 for a retainer 400 that includes a length that is less than or equal to approximately 75% of the length of the retainer 400 measured along the longitudinal axis 410. It will be appreciated, that, although not depicted in FIGS. 3A-3B, the center rib extension 420 of that example embodiment can include the sharp edge 422. As will be explained in further detail in FIGS. 4A-4B, the edge 422 aids the center rib extension 420 in splitting an implantable adjunct 300 into two separate halves 306, 308 when the retainer 400 is disposed on a staple cartridge 100.

It will also be appreciated that the retainer 400 of the staple cartridge 100 can be formed from stamped sheet metal or other materials as understood by one skilled in the pertinent art. The retainer 400 can further include a thickness between the range of approximately 0.007 inches and approximately 0.030 inches. Typically, retainers for staple cartridges can be made from a polycarbonate material that results in a thick retainer. Sterilization of other materials within the cartridges will also typically off gas oxygen in combination with the polycarbonate material of the retainer. However, a retainer comprising sheet metal and a thickness within the previously specified range of 0.007-0.030 inches would allow for easier assembly of a retainer onto a staple cartridge due to its thinner, yet sturdy composition as well as eliminate oxygen off gassing by removing the polycarbonate as a whole.

Figure 4A:
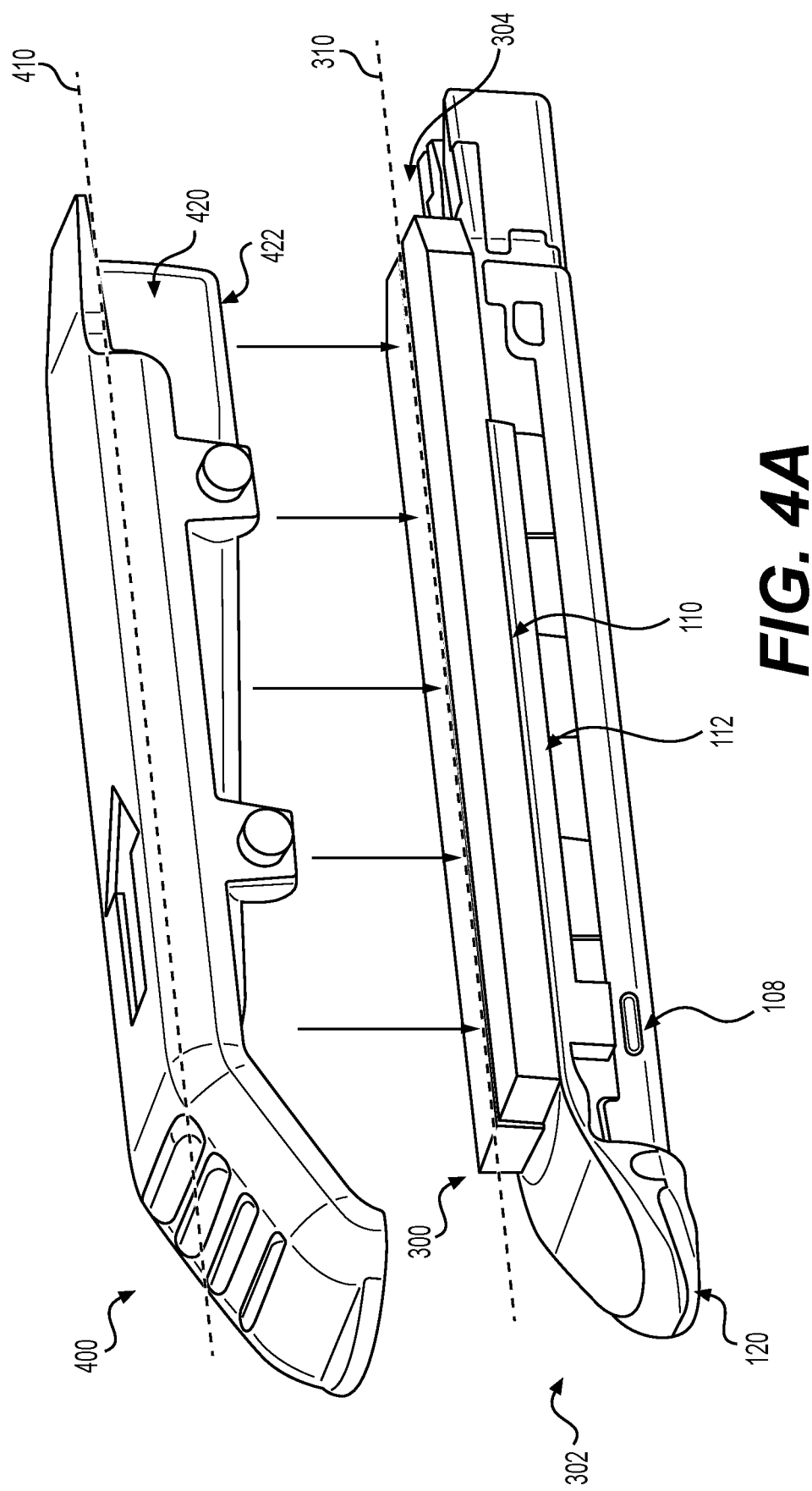
FIG. 4A is a perspective view of a retainer and staple cartridge comprising an implantable adjunct prior to the installation of the retainer, according to aspects of the present invention.
Figure 4B:
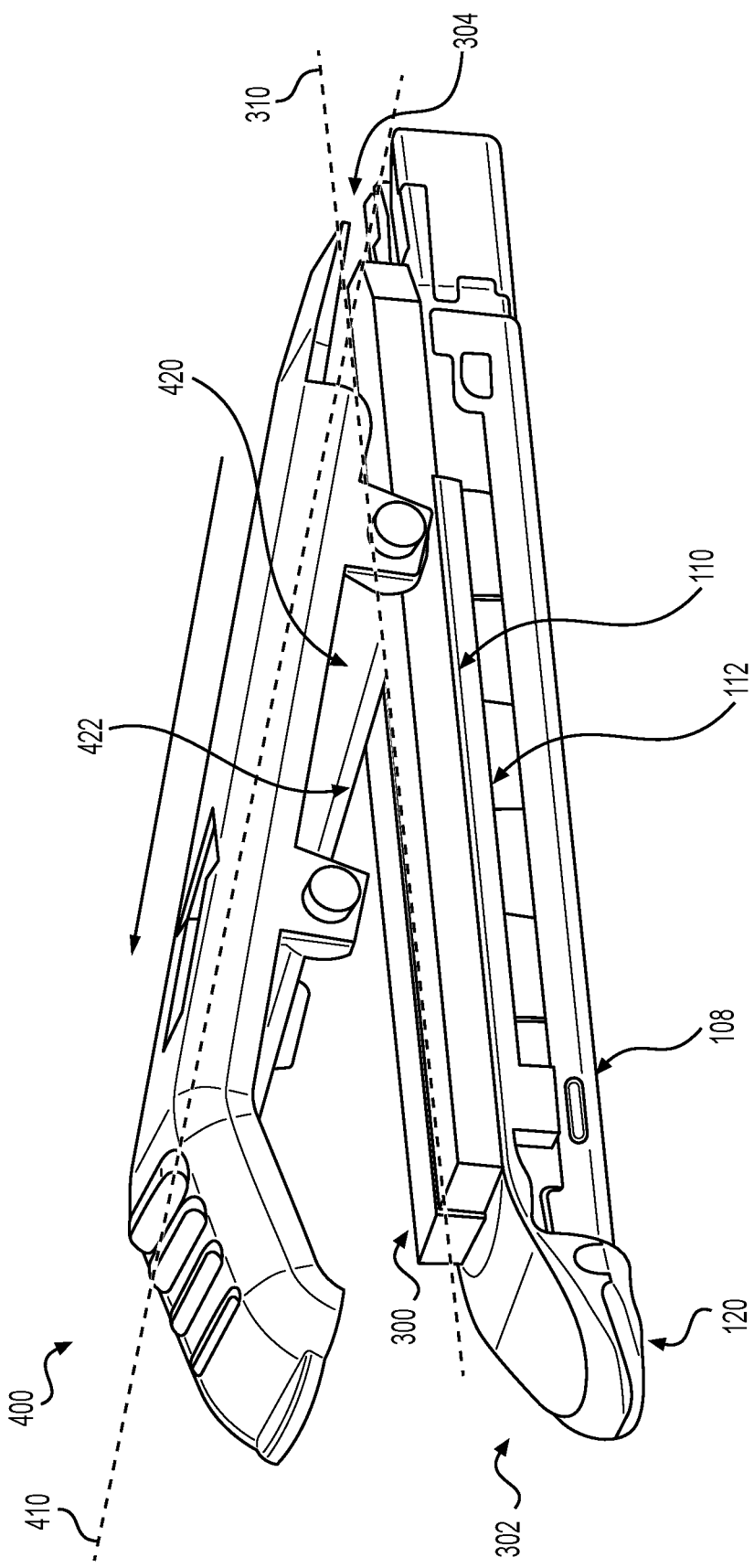
FIG. 4B is a perspective view of the retainer and staple cartridge from FIG. 4A being removed from the staple cartridge at an angle and splitting the implantable adjunct, according to aspects of the present invention.

Turning now to FIGS. 4A-4B, an example staple cartridge 100 including a retainer 400 prior to connection to the staple cartridge 100 can be seen. As explained above, the staple cartridge 100 includes an elongate body 120 and an implantable adjunct 300 disposed on a deck 108 of the elongate body 120. The implantable adjunct 300 is disposed over a plurality of staple pockets 110 that are accessible via openings 112 defined by the deck 108. The implantable adjunct 300 includes a distal end 302, a proximal end 304, and a knife slot 340 positioned along the length of a longitudinal axis 310 of the implantable adjunct 300 and is compressed when disposed on the deck 108 of the staple cartridge 100. The retainer 400 includes a center rib extension 420 positioned along a longitudinal axis 410 of the retainer 400. As can be seen in FIG. 4A, the retainer 400 is to be placed over the implantable adjunct 300, the center rib extension 420 of the retainer 400 comprising a sharp edge 422 that tapers on both sides that is to be placed against the knife slot 340 of the implantable adjunct 300.

FIG. 4B illustrates the retainer 400 of FIG. 4A being removed from the staple cartridge 100 at an angle. As can be seen, the center rib extension 420 of the retainer 400 is configured to split the implantable adjunct 300 into two halves 306, 308 using the sharp edge 422 of the center rib extension 420 to sever any connections between the two halves 306, 308. This is due, in part, to the sharp edge 422 of the center rib extension 420, but also due to the knife slot 340 of the implantable adjunct 300. The knife slot 340 comprises a plurality of slits 350 such that, when a sharp edge is applied to the knife slot 340, the plurality of slits 350 will easily break apart, thus resulting in two halves 306, 308 of an implantable adjunct 300.

FIGS. 5A-5B show a top view of the implantable adjunct 300 both before and after compression of the adjunct 300 respectively. FIG. 5A shows an implantable adjunct 300 that has had openings cut along a knife slot 340 down the center of the adjunct 300. These openings, also referred to as slits 350, can be made in several different ways. For example, and not limitation, they can be die-cut with a standard rule die, laser die, roller die, waterjet, etc. As explained above and in further detail below, the implantable adjunct 300 includes a distal end 302 and a tapered proximal end 304, the tapered proximal end 304 comprising a distal end 316 and a proximal end 318. The distal end 316 of the tapered proximal end 304 comprises a width that is greater than a width at the proximal end 318 of the tapered proximal end 304. The implantable adjunct 300 further includes a longitudinal axis 310 and a knife slot 340 disposed along the longitudinal axis and running parallel to the longitudinal axis 310. The knife slot 340 comprises a plurality of slits 350 that, prior to the compression of the implantable adjunct 300, have a first width 332 that is larger than a width of a center rib extension 420 of a retainer 400, further illustrated in FIGS. 3A-3C.

FIG. 5B illustrates the implantable adjunct 300 of FIG. 5A after it has been compressed and prior to its disposal on a deck 108 of a staple cartridge 100. As a result of the compression, each slit 350 of the plurality of slits 350 now comprises a second width 334 that is smaller than the first width 332 of the implantable adjunct shown in FIG. 5A. As will be appreciated, the implantable adjunct 300 can comprise alternate geometrical configurations provided they possess a generally rectangular composition. For example, and not limitation, the implantable adjunct can also include a completely rectangular composition with the distal and proximal ends having approximately equal width, as can be seen in FIG. 1. This example embodiments and alternate configurations can be applied and understood by one ordinarily skilled in the pertinent art.

FIG. 6 is a flowchart for an example method 600 of producing an implantable adjunct 300. The method 600 includes assembling 602 an implantable adjunct onto a deck 108 of an elongate body 120, the implantable adjunct 300 comprising a distal end 302 and a tapered proximal end 304, the tapered proximal end 304 having a width that is wider at a distal end 316 of the tapered proximal end 304 than the width at a proximal end 318 of the tapered proximal end 304. The method 600 further includes cutting 604 a knife slot 340 comprising a plurality of slits 350 in the implantable adjunct 300 to define a perforation 342 along a longitudinal axis 310 that extends the length of the implantable adjunct 300. The knife slot 340 can be formed in several different ways. For example, and not limitation, they can be die-cut with a standard rule die, laser die, roller die, waterjet, etc. The knife slot 340 comprises a first width 332 that is larger than the width of a center rib extension of a retainer 400. The method 600 further includes compressing 606 the implantable adjunct 300 such that the knife slot 340 has a second width 334 that is smaller than the first width 332 of the knife slot 340. This step can be illustrated between FIGS. 5A and 5B.

The method 600 further includes the step of cutting a transverse cut 360 at a proximal end 354 of a distal-most slit 352 of the knife slot 340 such that the transverse cut 360 transversely intersects the longitudinal axis 310 of the implantable adjunct 300. The method 600 can further include cutting additional transverse cuts 360 at the proximal ends 354 of each slit 350 of the plurality of slits 350. The method 600 can instead include cutting the transverse cuts 360 at the proximal end 354 of the distal-most slit 352 of the knife slot 340 such that the transverse cut 360, mirrored on either side of the longitudinal axis 310, is positioned at an angle that ranges approximately from 70 to 89 degrees when measured from the longitudinal axis 310 of the implantable adjunct 300. The transverse cuts 360 can be cut at some or all of the slits 350, depending on the desired result.

Examples of the present disclosure can be implemented by any of the following numbered clauses:

Clause 1: A staple cartridge (100), comprising: an elongate body (120), the elongate body (120) comprising a deck (108), the elongate body (120) defining a plurality of staple pockets (110), each of the staple pockets (110) accessible via an opening (112) defined by the deck (108); and an implantable adjunct (300) disposed on the deck (108) of the elongate body (120) comprising a distal end (302), a proximal end (304), and a knife slot (340) positioned along a longitudinal axis (310) of the implantable adjunct (300); wherein the knife slot (340) comprises a plurality of slits (350) defining a perforation in the implantable adjunct and a transverse cut (360) transversely intersecting a distal most slit (352) of the plurality of slits at a proximal end (354) of the distal most slit (352) of the knife slot (340).

Clause 2: The staple cartridge (100) of clause 1, wherein opposing walls defining the plurality of slits (350) of the knife slot (340) are configured to touch when the implantable adjunct (300) is disposed on the deck (108) of the staple cartridge (100).

Clause 3: The staple cartridge (100) of any one of the preceding clauses, wherein the perforation (342) further comprises additional transverse cuts (360) transversely intersecting the longitudinal axis (310) of the implantable adjunct (300) and positioned at the proximal ends (354) of each slit (350) of the perforation (342).

Clause 4: The staple cartridge (100) of any one of the preceding clauses, wherein the perforation (342) comprises a transverse cut (360) at the proximal end (354) of the distal-most slit (352) having an angle measured from the longitudinal axis (310) that ranges approximately from 70 to 89 degrees.

Clause 5: The staple cartridge (100) of any one of the preceding clauses, wherein the perforation (342) comprises additional transverse cuts (360) positioned at the proximal ends (354) of each slit (350), each of the additional transverse cuts (360) having an angle that ranges approximately from 70 to 89 degrees.

Clause 6: The staple cartridge (100) of any one of the preceding clauses, wherein the knife slot (340) of the implantable adjunct (300) comprises a width that is a predetermined distance greater than zero before the implantable adjunct (300) is disposed on the deck (108) of the elongate body (120).

Clause 7: The staple cartridge (100) of any one of the preceding clauses, wherein the staple cartridge (100) further comprises a retainer (400), the retainer (400) removably connected to the elongate body (120), the retainer (400) comprising a distal end (402), a proximal end (404), and a center rib extension (420) extending along a longitudinal axis (410) of the retainer (400).

Clause 8: The staple cartridge (100) of clause 7, wherein the implantable adjunct (300) is disposed between the retainer (400) and the deck (108) of the staple cartridge (100).

Clause 9: The staple cartridge (100) of clauses 7-8, wherein the center rib extension (420) is configured to separate the implantable adjunct (300) into two halves (306,308) when the adjunct (300) is compressed, and the retainer (400) is connected to the staple cartridge (100) assembly.

Clause 10: The staple cartridge (100) of clauses 7-9, wherein the center rib extension (420) connected to the retainer (400) of the staple cartridge (100) comprises a length less than or equal to 25% of the length of the retainer (400).

Clause 11: The staple cartridge (100) of clauses 7-10, wherein the center rib extension (420) further comprises an edge (422) that tapers on both sides of the center rib extension (420) to form a sharp edge along the length of the center rib extension (420).

Clause 12: The staple cartridge (100) of clause 7, wherein the center rib extension (420) is connected to the retainer (400) along the longitudinal axis (410) of the retainer (400) via two alignment tabs (424) connected to two openings (426) formed along the longitudinal axis (410) of the retainer (400) and adjacent to the distal end (402) of the retainer (400).

Clause 13: The staple cartridge (100) of clauses 7 and 12, wherein the center rib extension (420) connected to the retainer (400) of the staple cartridge (100) comprises a length at least 75% of the length of the retainer (400).

Clause 14: The staple cartridge (100) of clauses 7-13, wherein the retainer (400) is comprised of a sheet metal and has a thickness between 0.007 in and 0.030 in.

Clause 15: The staple cartridge (100) of any one of the preceding clauses, wherein the implantable adjunct (300) is configured to compensate for a varying thickness of target tissue of a patient that is being stapled and comprises a bio-degradable material.

Clause 16: A method for producing an implantable adjunct (300), the method comprising the steps of: assembling an implantable adjunct (300) onto a deck (108) of an elongate body (120), the implantable adjunct (300) comprising a distal end (302) and a tapered proximal end (304), the tapered proximal end (304) having a width that is wider at a distal end (316) of the tapered proximal end (304) than the width at a proximal end (318) of the tapered proximal end (304); (602) cutting a knife slot (340) comprising a plurality of slits (350) in the implantable adjunct (300) to define a perforation (342) along a longitudinal axis (310) that extends the length of the implantable adjunct (300), the knife slot (340) comprising a first width (332), the first width being larger than the width of a center rib extension (420) of a retainer (400); (604) and compressing the implantable adjunct (300) such that the knife slot (340) has a second width (334), the second width of the knife slot (340) being smaller than the first width of the knife slot (340). (606)

Clause 17: The method of clause 16, the method further comprising the step of: cutting a transverse cut (360) transversely intersecting the longitudinal axis (310) of the implantable adjunct (300) and positioned at a proximal end (354) of a distal-most slit (352) of the knife slot (340).

Clause 18: The method of clause 17, the method further comprising the step of: cutting additional transverse cuts (360) transversely intersecting the longitudinal axis (310) of the implantable adjunct (300) and positioned at the proximal ends (354) of each slit (350) of the knife slot (340).

Clause 19: The method of clause 16, the method further comprising the steps of: cutting a transverse cut (360) at the proximal end (354) of the distal-most slit (350) and having an angle measured from the longitudinal axis (310) that ranges approximately from 70 to 89 degrees.

Clause 20: The method of clause 19, the method further comprising the steps of: cutting additional transverse cuts (360) at the proximal ends of the slits (350) and having an angle measured from the longitudinal axis (310) that ranges approximately from 70 to 89 degrees.

Clause 21: An implantable adjunct (300) for use with a staple cartridge (100), the implantable adjunct (300) comprising: a distal end (302) comprising a constant width along a major length of the distal end; a tapered proximal end (304) comprising a distal end (316) and a proximal end (318), and having a width at the distal end (316) of the tapered proximal end (304) that is wider than a width at the proximal end (318) of the tapered proximal end (304); and a knife slot (340) disposed within the implantable adjunct (300) and positioned along a longitudinal axis (310) of the implantable adjunct (300), the knife slot configured to have a width that is a predetermined distance greater than zero; and wherein the implantable adjunct (300) is configured to compensate for a varying thickness of target tissue of a patient that is being stapled and comprises a bio-degradable material.

Clause 22: The implantable adjunct (300) of clause 21, wherein the knife slot (340) further comprises a perforation (342) across the entire length of the knife slot (340) and defining several slits (350) along the perforation (342), opposing walls defining the slits (350) configured to touch when the implantable adjunct (300) is disposed on a deck (108) of a staple cartridge (100).

Clause 23: The implantable adjunct (300) of clause 22, wherein the knife slot (340) further comprises a transverse cut (360) transversely intersecting the longitudinal axis (310) of the implantable adjunct (300) and positioned at a proximal end (354) of a distal-most slit (352) of the knife slot (340).

Clause 24: The implantable adjunct (300) of clause 23, wherein the knife slot (340) further comprises additional transverse cuts (360) transversely intersecting the longitudinal axis (310) of the implantable adjunct (300) and positioned at the proximal ends of each slit (350) of the knife slot (340).

Clause 25: The implantable adjunct (300) of clause 22, wherein the knife slot (340) further comprises a transverse cut (360) positioned at a proximal end (354) of a distal-most slit (352) of the knife slot (340) and having an angle measured from the longitudinal axis (310) that ranges approximately from 70 to 89 degrees.

Clause 26: The implantable adjunct (300) of clause 25, wherein the knife slot (340) further comprises additional transverse cuts (360) positioned at the proximal ends (354) of the slits (350) of the knife slot (340) and having an angle measured from the longitudinal axis (310) that ranges approximately from 70 to 89 degrees.

In describing example embodiments, terminology has been resorted to for the sake of clarity. As a result, not all possible combinations have been listed, and such variants are often apparent to those of skill in the art and are intended to be within the scope of the claims which follow. It is intended that each term contemplates its broadest meaning as understood by those skilled in the art and includes all technical equivalents that operate in a similar manner to accomplish a similar purpose without departing from the scope and spirit of the invention. It is also to be understood that the mention of one or more steps of a method does not preclude the presence of additional method steps or intervening method steps between those steps expressly identified. Similarly, some steps of a method can be performed in a different order than those described herein without departing from the scope of the disclosed technology.

What is claimed is:

1. A staple cartridge, comprising:
    an elongate body, the elongate body comprising a deck, the elongate body defining a plurality of staple pockets, each of the staple pockets accessible via an opening defined by the deck; and
    an implantable adjunct disposed on the deck of the elongate body comprising a distal end, a proximal end, and a knife slot positioned along a longitudinal axis of the implantable adjunct;
    wherein the knife slot comprises a plurality of slits defining a perforation in the implantable adjunct and a transverse cut transversely intersecting a distal most slit of the plurality of slits at a proximal end of the distal most slit of the knife slot.

2. The staple cartridge of claim 1, wherein opposing walls defining the plurality of slits of the knife slot are configured to touch when the implantable adjunct is disposed on the deck of the staple cartridge.

3. The staple cartridge of claim 1, wherein the perforation further comprises additional transverse cuts transversely intersecting the longitudinal axis of the implantable adjunct and positioned at the proximal ends of each slit of the perforation.

4. The staple cartridge of claim 1, wherein the perforation comprises a transverse cut at the proximal end of the distal-most slit having an angle measured from the longitudinal axis that ranges approximately from 70 to 89 degrees.

5. The staple cartridge of claim 4, wherein the perforation comprises additional transverse cuts positioned at the proximal ends of each slit, each of the additional transverse cuts having an angle that ranges approximately from 70 to 89 degrees.

6. The staple cartridge of claim 1, wherein the knife slot of the implantable adjunct comprises a width that is a predetermined distance greater than zero before the implantable adjunct is disposed on the deck of the elongate body.

7. The staple cartridge of claim 1, wherein the staple cartridge further comprises a retainer, the retainer removably connected to the elongate body, the retainer comprising a distal end, a proximal end, and a center rib extension extending along a longitudinal axis of the retainer.

8. The staple cartridge of claim 7, wherein the implantable adjunct is disposed between the retainer and the deck of the staple cartridge.

9. The staple cartridge of claim 7, wherein the center rib extension is configured to separate the implantable adjunct into two halves when the adjunct is compressed, and the retainer is connected to the staple cartridge assembly.

10. The staple cartridge of claim 7, wherein the center rib extension connected to the retainer of the staple cartridge comprises a length less than or equal to 25% of the length of the retainer.

11. The staple cartridge of claim 7, wherein the center rib extension further comprises an edge that tapers on both sides of the center rib extension to form a sharp edge along the length of the center rib extension.

12. The staple cartridge of claim 7, wherein the center rib extension is connected to the retainer along the longitudinal axis of the retainer via two alignment tabs connected to two openings formed along the longitudinal axis of the retainer and adjacent to the distal end of the retainer.

13. The staple cartridge of claim 7, wherein the center rib extension connected to the retainer of the staple cartridge comprises a length at least 75% of the length of the retainer.

14. The staple cartridge of claim 7, wherein the retainer is comprised of a sheet metal and has a thickness between 0.007 in and 0.030 in.

15. The staple cartridge of claim 7, wherein the implantable adjunct is configured to compensate for a varying thickness of target tissue of a patient that is being stapled and comprises a bio-degradable material.

16. A method for producing an implantable adjunct, the method comprising the steps of:
    assembling an implantable adjunct onto a deck of an elongate body, the implantable adjunct comprising a distal end and a tapered proximal end, the tapered proximal end having a width that is wider at a distal end of the tapered proximal end than the width at a proximal end of the tapered proximal end;

cutting a knife slot comprising a plurality of slits in the implantable adjunct to define a perforation along a longitudinal axis that extends the length of the implantable adjunct, the knife slot comprising a first width, the first width being larger than the width of a center rib extension of a retainer; and compressing the implantable adjunct such that the knife slot has a second width, the second width of the knife slot being smaller than the first width of the knife slot.

17. The method of claim 16, the method further comprising the step of: cutting a transverse cut transversely intersecting the longitudinal axis of the implantable adjunct and positioned at a proximal end of a distal-most slit of the knife slot.

18. The method of claim 17, the method further comprising the step of: cutting additional transverse cuts transversely intersecting the longitudinal axis of the implantable adjunct and positioned at the proximal ends of each slit of the knife slot.

19. The method of claim 16, the method further comprising the steps of: cutting a transverse cut at the proximal end of the distal-most slit and having an angle measured from the longitudinal axis that ranges approximately from 70 to 89 degrees.

20. The method of claim 19, the method further comprising the steps of: cutting additional transverse cuts at the proximal ends of the slits and having an angle measured from the longitudinal axis that ranges approximately from 70 to 89 degrees.

* * * * *